12) United States Patent
Nagata

(10) Patent No.: US 8,603,455 B2
(45) Date of Patent: Dec. 10, 2013

(54) REMOVAL PROMOTERS AND INHIBITOR FOR APOPTOSIS CELLS IN VIVO

(75) Inventor: Shigekazu Nagata, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 260 days.

(21) Appl. No.: 12/457,423

(22) Filed: Jun. 10, 2009

(65) Prior Publication Data

US 2010/0136100 A1 Jun. 3, 2010

Related U.S. Application Data

(62) Division of application No. 11/984,033, filed on Nov. 13, 2007, now abandoned, which is a division of application No. 10/496,087, filed as application No. PCT/JP02/12053 on Nov. 19, 2002, now abandoned.

(30) Foreign Application Priority Data

Nov. 20, 2001 (JP) ................................. 2001-354282

(51) Int. Cl.
*C07K 5/00* (2006.01)
(52) U.S. Cl.
USPC ......................................... 424/85.1; 530/350
(58) Field of Classification Search
None
See application file for complete search history.

(56) References Cited

U.S. PATENT DOCUMENTS 5,595,756 A * 1/1997 Bally et al. ..................... 424/450
2010/0136100 A1 * 6/2010 Nagata ............................ 424/450

FOREIGN PATENT DOCUMENTS

EP 1004664 A1 * 5/2000
WO WO 99/42564 8/1999
WO WO 00/30667 6/2000

OTHER PUBLICATIONS

Proesmans et al., What's new in cystic fibrosis? From treating symptoms to correction of the basic defect, Eur J Pediatr. 167(8):839-49, 2008.*
Riordan, CFTR Function and Prospects for Therapy. Annu Rev Biochem. 77:701-26, 2008.*
Asano et al., Masking of Phosphatidylserine Inhibits Apoptotic Cell Engulfment and Induces Autoantibody Production in Mice, J. Exp. Med. 200(4):459-67, 2004.*
Chaoyong Ma Animal models of disease Modern Drug Discovery 2004, 7 (6).*
Couto et al., Cloning and sequence analysis of human breast epithelial antigen BA46 reveals an RGD cell adhesion sequence presented on an epidermal growth factor-like domain, DNA Cell Biol. 15(4):281-286, 1996.*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Drakopanagiotakis et al., Apoptosis in lung injury and fibrosis, Eur Respir J. 32(6):1631-8, 2008.*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Andersen, Mikkel H. et al., "Functional Analyses of Two Cellular Binding Domains of Bovine Lactadherin", Biochemistry, vol. 39, No. 20, May 23, 2000, pp. 6200-6206.
Ezekowitz, R. Alan, "Local Opsonization for Apoptosis", Nature Immunology, vol. 3, No. 6, Jun. 2002, pp. 510-512.
Schlegel, Robert A. et al., "CD14 is a Component of Multiple Recognition Systems used by Macrophages to Phagocytose Apoptotic Lymphocytes", Cell Death and Differentiation, vol. 6, No. 6, Jun. 1999, pp. 583-592.
Théry, Clotilde et al., "Molecular Characterization of Dendritic Cell-derived Exosomes. Selective Accumulation of the Heat Shock Protein hsc73", The Journal of Cell Biology, vol. 147, No. 3, Nov. 1999, pp. 599-610.
Colin Collins, et al., "Mapping of a Newly Discovered Human Gene Homologous to the Apoptosis Associated-Murine Mammary Protein, MFG-E8, to Chromosome 15q25", GENOMICS, 1997, pp. 117-118, vol. 39, No. 1.
Rikinari Hanayama et al., "Identification of a factor that links apoptotic cells to phagocytes", Nature, May 2002, pp. 182-187, vol. 417, No. 6885.
Stubbs et al., 1990, PNAS, vol. 87 p. 8417-8421.
Rudinger, 1976, Peptide Hormones, Parsons, University Park Press, Baltimore, p. 1-7.
Kaye et al., 1990, Proc, Natl. Acad. Sci. USA, vol. 87, pp. 6922-6926.
Davis, C. G., 1990, The New Biologist, vol. 2, No. 5, p. 410-419.
Skolnick et al., 2000, Trends in Biotech, vol. 18, p. 34-39.

(Continued)

*Primary Examiner* — Brian J Gangle
*Assistant Examiner* — Andrea McCollum
(74) *Attorney, Agent, or Firm* — Foley & Lardner LLP

(57) ABSTRACT

The present invention is to provide a removal promoter for apoptotic cells which is capable of immediately removing apoptotic cells in vivo by macrophages, or a removal inhibitor which inhibits the removal of apoptotic cells in vivo by macrophages. A removal promoter for apoptotic cells in vivo containing the milk fat globule-EGF factor 8-L (MFG-E8-L), MFG-E8-L mutant having removal promotion action for apoptotic cells in vivo by macrophages, or preferably a recombinant human or mouse MFG-E8-L, or a recombinant human or mouse MFG-E8-L mutant as an active ingredient is prepared. Such removal promoters specifically bind to apoptotic cells and promote the phagocytosis of apoptotic cells by macrophages by recognizing aminophospholipids such as phosphatidylserine exposed on apoptotic cell surface. On the other hand, a point mutation (D89E) MFG-E8-L mutant is used as a removal inhibitor.

3 Claims, 12 Drawing Sheets

(56) References Cited

OTHER PUBLICATIONS

Aoik et al., Molecular cloning of glycoprotein antigens MGP57/53 recognized by monoclonal antibodies raised against bovine milk fat globule membrane, Biochim Biophys Acta. 1245(3):385-91, 1995.

Ishizaka, IgE-binding factors and regulation of the IgE antibody response, Annu Rev Immunol. 6:513-34, 1988.

Hanayama et al., "Identification of a factor that links apoptotic cells to phagocytes," Nature, May 9, 2002, 417(6885)182-187.

Taylor et al., "Lactadherin (Formerly BA46), a Membrane-Associated Glycoprotein Expressed in Human Milk and Breast Carcinomas, Promotes Arg-Gly-Asp (RGD)-Dependent Cell Adhesion," DNA and Cell Biology, 1997, 16(7):861-869.

* cited by examiner

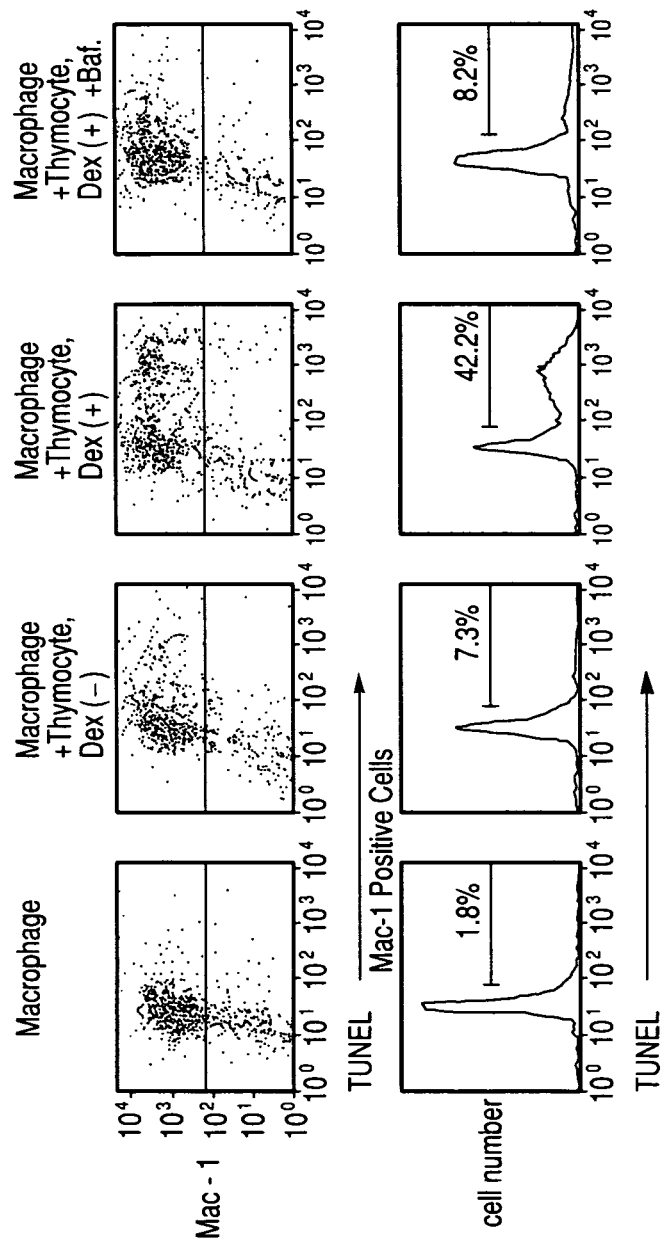

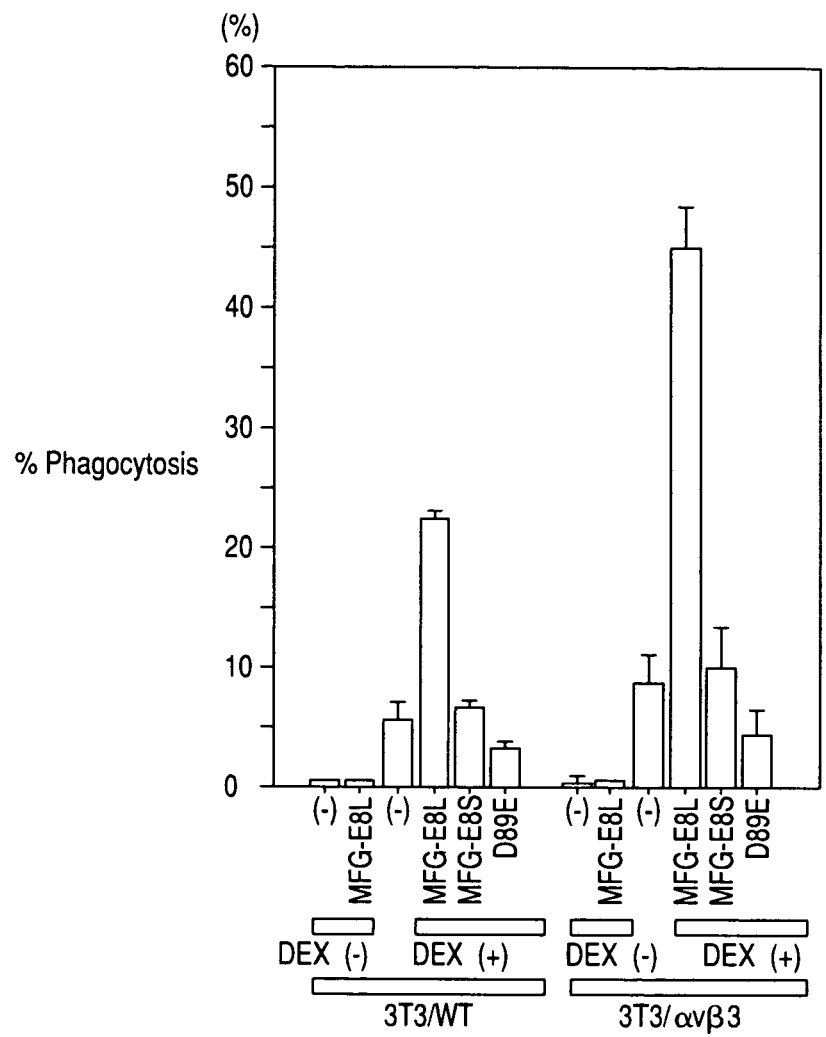

REMOVAL PROMOTERS AND INHIBITOR FOR APOPTOSIS CELLS IN VIVO

This application is a divisional application of application Ser. No. 11/984,033, filed Nov. 13, 2007, which is a divisional application of application Ser. No. 10/496,087, filed Nov. 9, 2004, which is the National Stage Application of International Application PCT/JP02/12053, filed Nov. 19, 2002, which claims the priority to Japan Application No. 2001-354282, filed Nov. 20, 2001, which are incorporated herein by reference in their entirety.

TECHNICAL FIELD

The present invention relates to compounds that promote or inhibit the engulfment of cells undergoing apoptosis (hereinafter referred to as 'apoptotic cells') by macrophages in vivo.

BACKGROUND ART

Cell death programmed that the cell itself is to positively bring about death under the physiological condition, namely apoptosis, is known to be a mechanism equipped to a living body in order to remove aging cells in immune system and unfavorable cells for the living body such as morbid cells. Such apoptosis is characterized in rapid contraction in cell size and change in a cell nucleus, apoptotic cells usually become apoptotic bodies and are to be finally engulfed by phagocytes such as macrophages and the like. For instance, it is well known that cells first contract and detach from adjacent cells, a chromatin which is a complex of DNA of nucleus and protein is compressed around a nuclear membrane to cause concentration of nucleus, and microvillus on the cell surface is vanished and smoothed at the same time, a protuberances of various sizes appear and they will gradually be constricted and torn apart, then fractionated into globular apoptotic bodies of various sizes enveloped in membrane, and such bodies are engulfed and eliminated by macrophages or adjacent phagocytes.

In the meantime, synthetic materials such as aminopterin, methotrexate, 8-azaguanine, 6-mercaptopurine, 5-fluorouracil, 1-(2-tetrahydrofuryl)-5-fluorouracil, etc., and antibiotics such as mitomycin C, chromomycin, bleomycin, etc., interferon, CSF inhibitor, CBF, etc., are known to be used to inhibit the proliferation of morbid cells such as cancer cells and malignant tumor cells and to treat diseases resulting from these cells. All of them act to a certain cell and cause necrosis to remove morbid cells. Unlike necrosis, which occurs by pathological factor, apoptosis is known to occur not only by pathological factor but also by various physiological factors.

It is reported that apoptosis is accompanied by sequence change of the cell membrane phospholipids which comprise a cell in the early stage, and results in the exposure to the cell surface of phosphatidylserine which is a negatively-charged phospholipid (Immunol. Today, 14:131-136, 1993; Cirk. Res., 77:1136-1142, 1995). It is considered that these changes on the cell surface are recognized by macrophages and adjacent cells, and phagocytic stages proceed. It is considered that the exposure of phosphatidylserine to the cell surface of apoptotic cells plays an important role in phagocytic mechanism since the above-mentioned phagocytic stages are inhibited by annexin V which selectively binds to phosphatidylserine (Biochem. Biophys. Res. Commun., 205: 1488-1493, 1994; Proc. Natl. Acad. Sci. USA, 93:1624-1629, 1996). Besides, detection of early stage of apoptosis is conducted by flowcytometry using labeled body of annexin V.

On the other hand, MFG-E8: milk fat globule-EGF factor 8 is cloned as a secretory protein derived from mammary epithelia abundantly contained in breast milk (Biochem. Biophys. Res. Commun. 254 (3), 522-528, 1999), which is known as a secretory glycoprotein strongly expressing in many other normal tissues or several tumor cells afterwards. MFG-E8 is comprised of two EGF (epidermal growth factor) domains from N termini side and a domain which has homology with C1 and C2 domains of a blood coagulation factor V and VIII. Homology of MFG-E8 is reported in several mammals including humans (BA46, lactadherin), mice (MFG-E8), rats (rAGS), pigs (P47), cows (PAS-6, PAS-7), and endothelial cell-specific cell adhesion molecule DELI which has similarity in domain structure with MFG-E8 has been cloned, further, MFG-E8 and DELI contain RGD sequence which binds to integrin in their second EGF domain. Besides, C1 and C2 domains of C termini side are known to bind to phospholipids on cell membrane. However, many points regarding the relation with enzymatic activity and its physiological function of MFG-E8 are still unknown. In order to clear these points, genomic gene of mouse milk fat globule-EGF factor 8 MFG-E8 and chromosome mapping, kinetics of gene expression in development stage, intracellular localization and the like have been considered, and it is recognized that reproductive rudiment is a main expression part at the early development stage of MFG-E8, and there is a strong expression characteristic to neuron or cartilage rudiment at a later development stage. Further, attempts have been made to generate MFG-E8 gene deficient mouse in order to investigate the function of MFG-E8 in vivo.

Apoptosis plays an important role in maintaining the homeostasis of living body. It is necessary to remove apoptotic cells immediately by macrophages in order to protect normal cells from noxious substance secreted by the cells undergoing apoptosis (apoptotic cells). For instance, cancer can be treated by positively inducing apoptosis in cancer cells. Even in such case, however, it is necessary to remove apoptotic cells immediately. The object of the present invention is to provide a removal promoter for apoptotic cells which can immediately remove apoptotic cells in vivo by macrophages, and a removal inhibitor which inhibits the removal of apoptotic cells in vivo by macrophages.

As a result of keen study in order to solve the above-mentioned issues, the present inventors found that milk fat globule-EGF factor 8 (MFG-E8-L) binds specifically to apoptotic cells by recognizing aminophospholipid such as phosphatidylserine (PS) and the like which are exposed on the cell surface once the cells started to move toward apoptosis, and MFG-E8-L promote the phagocytosis of apoptotic cells by macrophages, and that D89E mutant which is a point mutant derivative of MFG-E8-L inhibits the phagocytosis of apoptotic cells by macrophages. Thus, the present invention has been completed.

DISCLOSURE OF THE INVENTION

The present invention relates to: a removal promoter for apoptotic cells in vivo by macrophages which contains MFG-E8-L as an active ingredient ("1"); a removal promoter for apoptotic cells in vivo by macrophages which is comprised of amino acid sequence wherein one or more amino acids are deleted, substituted or added in the amino acid sequence comprising MFG-E8-L, and which contains MFG-E8-L mutant having removal promotion action for apoptotic cells in vivo by macrophages as an active ingredient ("2"); the removal promoter for apoptotic cells in vivo by macrophages according to "1" or "2" wherein the MFG-E8-L or the MFG- E8-L mutant which has removal action for apoptotic cells is a recombinant MFG-E8-L or a recombinant MFG-E8-L mutant ("3"); the removal promoter for apoptotic cells in vivo by macrophages according to "3" wherein the recombinant MFG-E8-L or the recombinant MFG-E8-L mutant is a recombinant human or mouse MFG-E8-L, or a recombinant human or mouse MFG-E8-L mutant ("4"); the removal promoter for apoptotic cells in vivo by macrophages according to "3" or "4" wherein the recombinant MFG-E8-L or the recombinant MFG-E8-L mutant is a translation product in human cells ("5"); the removal promoter for apoptotic cells in vivo by macrophages according to any one of "3" to "5" wherein the recombinant MFG-E8-L or the recombinant MFG-E8-L mutant contains an EGF-2 domain having RGD motif, a proline/threonine-rich domain, and two factor VIII-homologous domains (C1 and C2) ("6").

The present invention further relates to: the removal promoter for apoptotic cells in vivo by macrophages according to any one of "1" to "6" wherein the MFG-E8-L or the MFG-E8-L mutant is enveloped or embedded in liposome ("7"); the removal promoter for apoptotic cells in vivo by macrophages which contains a recombinant vector including DNA encoding the MFG-E8-L or the MFG-E8-L mutant according to any one of "1" to "6" as an active ingredient ("8"); the removal promoter for apoptotic cells in vivo by macrophages which contains a host cell comprising the expression system which can express the MFG-E8-L or the MFG-E8-L mutant according to any one of "1" to "6" as an active ingredient ("9"); the removal promoter for apoptotic cells in vivo by macrophages which contains an antibody against the MFG-E8-L mutant according to any one of "1" to "6" as an active ingredient ("10"); the removal promoter for apoptotic cells in vivo by macrophages according to "10" wherein the antibody against the MFG-E8-L mutant according to any one of "1" to "6" is an anti-MFG-E8-L monoclonal antibody or an anti-MFG-E8-L mutant monoclonal antibody ("11").

The present invention still further relates to: a removal method for apoptotic cells in vivo by macrophages wherein the removal promoter for apoptotic cells in vivo according to any one of "1" to "11" is used ("12"); a therapeutic agent for diseases resulting from incomplete removal of apoptotic cells in vivo by macrophages which contains the removal promoter for apoptotic cells in vivo by macrophages according to any one of "1" to "11" ("13"); an enhancer for biodefense mechanism which contains the removal promoter for apoptotic cells in vivo according to any one of "1" to "11" ("14"); a therapeutic method for diseases resulting from incomplete removal of apoptotic cells in vivo by macrophages wherein the therapeutic agent according to "13" or the enhancer for biodefense mechanism according to "14" is used ("15").

The present invention also relates to: a removal inhibitor for apoptotic cells in vivo by macrophages comprised of amino acid sequence wherein one or more amino acids are deleted, substituted or added in the amino acid sequence comprising MFG-E8-L, and which contains a MFG-E8-L mutant having removal inhibition action for apoptotic cells in vivo by macrophages as an active ingredient ("16"); the removal inhibitor for apoptotic cells in vivo by macrophages according to "16" wherein the MFG-E8-L mutant having removal inhibition action for apoptotic cells is a recombinant MFG-E8-L mutant ("17"); the removal inhibitor for apoptotic cells in vivo by macrophages according to "17" wherein the recombinant MFG-E8-L mutant is a recombinant human MFG-E8-L mutant or a recombinant mouse MFG-E8-L mutant ("18"); the removal inhibitor for apoptotic cells in vivo by macrophages according to "17" or "18" wherein the recombinant MFG-E8-L mutant is a translation product in human cells ("19"); the removal inhibitor for apoptotic cells in vivo by macrophages according to any one of "17" to "19" wherein the recombinant MFG-E8-L mutant is a MFG-E8-L mutant which contains a proline/threonine-rich domain and two factor VIII-homologous domains (C1 and C2), and which has a point mutation in RGD motif ("20"); the removal inhibitor for apoptotic cells in vivo by macrophages according to "20" wherein the MFG-E8-L mutant which has a point mutation is D89E mutant ("21").

The present invention further relates to: the removal inhibitor for apoptotic cells in vivo by macrophages according to any one of "16" to "21" wherein the MFG-E8-L mutant is enveloped or embedded in liposome ("22"); the removal inhibitor for apoptotic cells in vivo by macrophages which contains a recombinant vector including DNA encoding the MFG-E8-L mutant according to any one of "16" to "21" as an active ingredient ("23"); the removal inhibitor for apoptotic cells in vivo by macrophages which contains a host cell comprising an expression system which can express the MFG-E8-L mutant according to any one of "16" to "21" as an active ingredient ("24"); a removal inhibition method for apoptotic cells in vivo by macrophages wherein the removal inhibitor for apoptotic cells in vivo according to any one of "16" to "24" is used ("25"); a therapeutic agent for diseases resulting from the incomplete removal inhibition of apoptotic cells in vivo by macrophages which contains the removal inhibitor for apoptotic cells in vivo according to any one of "16" to "24" ("26"); a therapeutic method for diseases resulting from the incomplete removal inhibition of apoptotic cells in vivo by macrophages wherein the therapeutic agent according to "26" is used ("27"); a detection agent for apoptotic cells in vivo which contains a labeled MFG-E8-L or MFG-E8-L mutant having removal promotion action for apoptotic cells in vivo by macrophages, or an antibody against them, or a labeled MFG-E8-L mutant having removal inhibition action for apoptotic cells in vivo by macrophages as an active ingredient ("28"); a detection method for apoptotic cells in vivo wherein a detection agent for apoptotic cells in vivo which contains a labeled MFG-E8-L or MFG-E8-L mutant having removal promotion action for apoptotic cells in vivo by macrophages, or an antibody against them, or a labeled MFG-E8-L mutant having removal inhibition action for apoptotic cells in vivo by macrophages as an active ingredient is used ("29"); a screening method for a removal promotion inducing substance or a removal promotion suppressive substance for apoptotic cells in vivo by macrophages wherein MFG-E8-L or a MFG-E8-L mutant having removal promotion action for apoptotic cells in vivo by macrophages, or an antibody against them is contacted with a test substance, to evaluate the extent of removal of apoptotic cells in vivo ("30"); a screening method for a removal inhibition inducing substance or a removal inhibition suppressive substance for apoptotic cells in vivo by macrophages wherein a MFG-E8-L mutant which has removal inhibition action for apoptotic cells in vivo by macrophages is contacted with a test substance, to evaluate the extent of removal inhibition of apoptotic cells in vivo ("31").

BRIEF DESCRIPTION OF DRAWINGS

FIG. 2 is a photograph showing the experimental results regarding the identification and the expression of MFG-E8.

FIG. 3 is a drawing showing the experimental results regarding the binding of MFG-E8 to aminophospholipids exposed on the apoptotic cells.

FIG. 4 is a drawing showing the experimental results regarding the binding of NIH3T3 cell to aminophospholipids via MFG-E8.

FIG. 5 is a photograph showing the experimental results regarding incorporation of apoptotic cells by MFG-E8-L. FIG. 5a shows the results of examining thymocyte incorporation by NIH3T3 cells, by incubating NIH3T3 (3T3/WT) or its transformant expressing $\alpha_v\beta_3$ integrin (3T3/$\alpha_v\beta_3$) in the absence (−) or presence of MFG-E8-L, MFG-E8-S, or D89E with thymocytes (Dex (−) or Dex (+)).

BEST MODE OF CARRYING OUT THE INVENTION

Figure 1A:
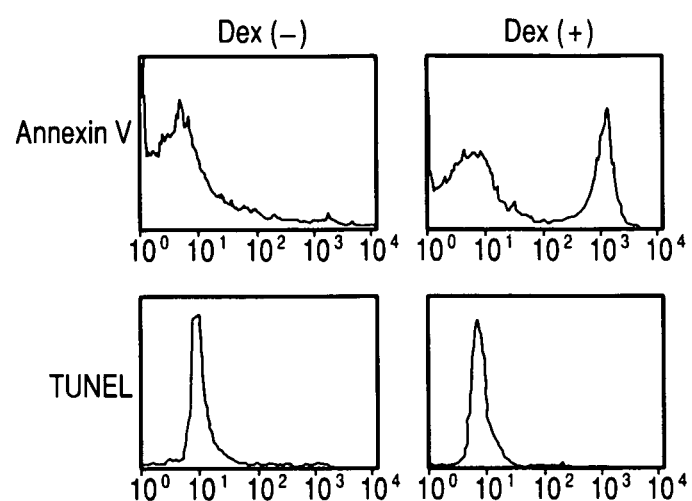
FIG. 1 is a photograph showing the experimental results regarding the establishment of a monoclonal antibody which increases the phagocytosis for apoptotic cells. F*ig*. 1*a* shows the results of Annexin V staining and TUNEL staining of the thymocytes from ICAD-Sdm mice that have been treated with dexamethasone. F*ig*. 1*b* shows the results of phycoerythrin-conjugated anti-Mac-1 antibody staining and TUNEL staining of thioglycollate-elicited mouse peritoneal macrophages after they were incubated with thymocytes from ICAD-Sdm mice.
FIG. 1c shows the analytical results of the effect of normal hamster IgG, or 2422 monoclonal antibody on the phagocytosis.
Fig. 1d is a photograph showing that apoptotic cells are engulfed by macrophages in the presence of 2422 monoclonal antibody.

As for a removal promoter for apoptotic cells in vivo by macrophages of the present invention, there is no particular limitation as long as it is comprised of milk fat globule-EGF factor 8-L (MFG-E8-L), or the amino acid sequence wherein one or more amino acids are deleted, substituted or added in the amino acid sequence comprising MFG-E8-L, and it contains MFG-E8-L mutant which has removal promotion action for apoptotic cells in vivo by macrophages as an active ingredient. The MFG-E8-L means herein a long chain MFG-E8 (a long form of MFG-E8), and for instance, mouse MFG-E8-L can be exemplified by MFG-E8-L comprised of 463 amino acid residues as shown in SEQ ID NO. 1 of the sequence list, and mouse MFG-E8-L mutant can, be further exemplified by MFG-E8-L mutant which is comprised of the amino acid sequence wherein one or more amino acids are deleted, substituted or added in the amino acid sequence shown by SEQ ID NO. 1, and which has removal promotion action for apoptotic cells in vivo by macrophages. The origin of the above-mentioned MFG-E8-L or MFG-E8-L mutant is not limited to mice, the MFG-E8-L or MFG-E8-L mutant derived from humans (also known as; BA46, lactadherin), rats (also known as; rAGS), pigs (also known as; P47), cows (also known as; PAS-6, PAS-7) and the like can also be used. However, human MFG-E8-L can be advantageously used for removal promotion of apoptotic cells in human living body by macrophages.

Further, as for the MFG-E8-L or MFG-E8-L mutant which has removal promotion action for apoptotic cells by macrophages, recombinant MFG-E8-L or recombinant MFG-E8-L mutant, or preferably, recombinant human MFG-E8-L or recombinant mouse MFG-E8-L, or recombinant human MFG-E8-L mutant or recombinant mouse MFG-E8-L mutant can be advantageously used. Such recombinant MFG-E8-L or recombinant MFG-E8-L mutant can be prepared by known method, however, it is preferable to be a product of genetic translation in human cells wherein a human cell is used as a host cell. The structure of MFG-E8-L includes a signal sequence, two EGF domains (EGF-1 and EGF-2 having RGD motif), a proline/threonine-rich domain (P/T-rich domain), and two factor VIII-homologous domains (C1 and C2), however, the one that has a EGF-2 domain having RGD motif, a proline/threonine-rich domain, and two factor VIII-homologous domains (C1 and C2) as recombinant MFG-E8-L or MFG-E8-L mutant which has removal promotion action for apoptotic cells by macrophages is preferable.

The removal promoter for apoptotic cells in vivo by macrophages of the present invention can be exemplified by a removal promoter for apoptotic cells in vivo wherein the above-mentioned MFG-E8-L or MFG-E8L mutant which has removal promotion action for apoptotic cells by macrophages is enveloped or embedded in liposome. The lipids constituting the liposome membrane can be eligibly exemplified by cationic liposome membrane such as dimethyl dioctadecyl ammonium bromide (DDAB), dioleoyl phosphatidylethanolamine (DOPE) and the like. It is also possible to make a monoclonal antibody, which selectively reacts to apoptotic cells such as anti-MFG-E8-L monoclonal antibody to be described hereinafter, bind to liposome membrane including the above-mentioned MFG-E8-L or MFG-E8-L mutant, and to use it as an immunoliposome.

The removal promoter for apoptotic cells in vivo by macrophages of the present invention can be further exemplified by a removal promoter for apoptotic cells in vivo which contains recombinant vector including the DNA encoding the above-mentioned MFG-E8-L or MFG-E8L mutant which has removal promotion action for apoptotic cells by macrophages as an active ingredient. As for the above-mentioned recombinant vector, there is no particular limitation as long as it is a vector including DNA encoding MFG-E8-L, for example, mouse MFG-E8 gene comprised of the base sequence shown by SEQ ID NO. 2, or DNA encoding MFG-E8-L mutant, however, the one including an expression system which is capable of expressing MFG-E8-L or MFG-E8-L mutant in a host cell is preferable; their examples include chromosome-, episome-, and virus-derived expression systems, or more particularly, vectors derived from bacterial plasmid, vectors derived from yeast plasmid, vectors derived from papovavirus such as SV40, vaccinia virus, adenovirus, chickenpox virus, pseudorabies virus, retrovirus, vectors derived from bacteriophage or transposon and vectors derived from the combination of these, e.g. vectors derived from genetic factors of plasmid and bacteriophage, such as cosmid and phagemid. The expression systems may contain control sequences that regulate as well as engender expression.

The removal promoter for apoptotic cells in vivo by macrophages of the present invention can be also exemplified by a removal promoter for apoptotic cells in vivo which contains a host cell comprising the expression system which is capable of expressing the above-mentioned MFG-E8-L or MFG-E8-L mutant which has removal promotion action for apoptotic cells by macrophages as an active ingredient. The DNA encoding MFG-E8-L or MFG-E8-L mutant, or a vector including such DNA can be introduced into a host cell by the methods described in many standard laboratory manuals such as manuals of Davis et al. (BASIC METHODS IN MOLECULAR BIOLOGY, 1986) and of Sambrook et al. (MOLECULAR CLONING: A LABORATORY MANUAL, $2^{nd}$ Ed., Cold Spring Harbor Laboratory Press, Cold Spring Harbor, N.Y., 1989), and the examples include calcium-phosphate transfection, DEAE-dextran-mediated transfection, transvection, microinjection, cationic lipid-mediated transfection, electroporation, transduction, scrape loading, ballistic introduction, infection, etc. The examples of host cells include bacterial prokaryotic cells such as *E. coli, Streptmyces, Bacillus Subtilis, Streptcoccus, Staphylococcus*, etc., eukaryotic cells such as yeast, *aspergillus*, etc., insect cells such as *Drosophila* S2, *Spodoptera* Sf9, etc., animal cells such as L cell, CHO cell, COS cell, HeLa cell, C127 cell, BALB/c3T3 cell (including mutants deficient in dihydrofolate reductase, tymidine kinase, etc.), BHK21 cell, HEK293 cell, Bowes malignant melanoma cell, etc. and plant cells or the like. However, human cells are preferable.

Further, the removal promoter for apoptotic cells in vivo by macrophages of the present invention can be exemplified by antibodies against MFG-E8-L or MFG-E8-L mutant which has removal promotion action for apoptotic cells in vivo by macrophages. Such antibodies can be particularly exemplified by immune-specific antibodies such as monoclonal antibodies, polyclonal antibodies, chimeric antibodies, single-stranded antibodies, humanized antibodies, etc. These antibodies can be generated by administering to an animal (preferably non-human) using the above-mentioned MFG-E8-L or MFG-E8-L mutant, or a part of them, or thioglycollate-elicited peritoneal macrophages as described in the examples, as an antigen, according to the conventional protocols. Among them, anti-MFG-E8-L monoclonal antibody or anti-MFG-E8-L mutant monoclonal antibody is preferable in view of its distinguished removal promotion action for apoptotic cells by macrophages. The monoclonal antibodies can be prepared, for instance, by any optional method such as a hybridoma method that brings antibodies produced by cultured materials of continuous cell line (Nature 256, 495-497, 1975), a trioma method, a human B-cell hybridoma method (Immunology Today 4, 72, 1983), an EBV-hybridoma method (MONOCLONAL ANTIBODIES AND CANCER THERAPY, pp. 77-96, Alan R. Liss, Inc., 1985), etc. Further, the preparation method for a single-chain antibody (U.S. Pat. No. 4,946,778) can be adopted to prepare a single-stranded antibody. Besides, transgenic mice, other mammals, etc., can be used for expressing humanized antibodies.

As for the removal method for apoptotic cells in vivo of the present invention, there is no particular limitation as long as it is a method wherein the above-mentioned removal promoter for apoptotic cells in vivo by macrophages is used. Besides, as for the therapeutic agent for diseases resulting from incomplete removal of apoptotic cells in vivo by macrophages or an enhancer for biodefense mechanism, there is no particular limitation as long as it contains the above-mentioned removal promoter for apoptotic cells in vivo by macrophages. Such diseases resulting from incomplete removal of apoptotic cells in vivo by macrophages can be exemplified by the diseases resulting from reduced apoptotic cells, such as various types of cancer, various types of autoimmune diseases, various types of viral diseases and the like. When the above-mentioned removal promoter for apoptotic cells in vivo is used as a therapeutic agent or an enhancer for biodefense mechanism, it is also possible to add various compound ingredients for dispensing such as ordinary carriers, binding agents, stabilizing agents, excipients, diluents, pH buffer, disintegrants, solubilizers, solubilizing agents, isotonic agents and the like, which are pharmaceutically accepted. Such therapeutic agent or enhancer for biodefense mechanism can be administered orally or parenterally. It is possible to administer parenterally in ordinary administration form, for instance, to inject the formulation such as solution, emulsion, suspending agent, etc. Or it is also possible to administer orally in the formulation of powder, granules, capsules, syrup, suspending agent, etc. For the case of oral administration, it is preferable to make the removal promoter for apoptotic cells in vivo a liposome-enveloped/embedded type as mentioned above. Further, as for the therapeutic method for diseases resulting from incomplete removal of apoptotic cells in vivo by macrophages of the present invention, there is no particular limitation as long as it is a therapeutic method wherein the above-mentioned therapeutic agent or enhancer for biodefense mechanism is used.

As for the removal inhibitor for apoptotic cells in vivo by macrophages of the present invention, there is no limitation as long as it is comprised of the amino acid sequence wherein one or more amino acids are deleted, substituted, or added in the amino acid sequence comprising MFG-E8-L, and which contains MFG-E8-L mutant which has removal inhibition action for apoptotic cells in vivo by macrophages as an active ingredient. However, as for the MFG-E8-L mutant which has removal inhibition action for apoptotic cells, recombinant MFG-E8-L mutant, preferably recombinant human MFG-E8-L mutant or recombinant mouse MFG-E8-L mutant can be advantageously used. Such recombinant MFG-E8-L mutant can be prepared according to a known method, however, it is preferable to be a product of genetic translation in human cells wherein human cells are used as host cells. As mentioned above, the structure of MFG-E8-L includes a signal sequence, two EGF domains (EGF-1, and EGF-2 having RGD motif), a proline/threonine-rich domain (P/T-rich domain), and two factor VIII-homologous domains (C1 and C2), however, MFG-E8-L mutant which has removal inhibition action for apoptotic cells can be eligibly exemplified by MFG-E8-L mutant which has a proline/threonine-rich domain, and two factor VIII-homologous domains (C1 and C2), and has a point mutation in RGD motif, for instance, D89 mutant wherein the $89^{th}$ amino acid D (aspartic acid) of mouse MFG-E8-L is substituted by E (glutamic acid).

As for the removal inhibitor for apoptotic cells in vivo of the present invention, it can be exemplified, as in the case of the above-mentioned removal promoter for apoptotic cells in vivo, by the above-mentioned removal inhibitor for apoptotic cells in vivo wherein MFG-E8-L mutant is enveloped or embedded in liposome, the above-mentioned removal inhibitor for apoptotic cells in vivo containing recombinant vector including the DNA encoding MFG-E8-L mutant as an active ingredient, or the above-mentioned removal inhibitor for apoptotic cells in vivo containing the host cell including the expression system which is capable of expressing MFG-E8-L mutant.

As for the removal inhibition method for apoptotic cells in vivo of the present invention, there is no particular limitation as long as it is a method wherein the above-mentioned removal inhibitor for apoptotic cells in vivo by macrophages of the present invention is used. There is no limitation either for the therapeutic agent or therapeutic method for diseases resulting from incomplete removal of apoptotic cells in vivo by macrophages of the present invention, as long as the removal inhibitor for apoptotic cells in vivo by macrophages is used therein.

As for the detection agent for apoptotic cells in vivo of the present invention, there is no limitation as long as it contains the above-mentioned MFG-E8-L or MFG-E8-L mutant which has removal promotion action for apoptotic cells in vivo by macrophages, or an antibody against them, or a labeled body of MFG-E8-L mutant which has removal promotion action for apoptotic cells in vivo by macrophages, namely, labeled MFG-E8-L, a labeled MFG-E8-L mutant having the in vivo apoptotic cell removal promotion action, an labeled anti-MFG-E8-L antibody, a labeled anti-MFG-E8-L mutant antibody having the in vivo apoptotic cell removal promotion action, a labeled MFG-E8-L mutant having the in vivo apoptotic cells removal inhibition action, as an active ingredient. The above-mentioned labeling body can be particularly exemplified by the above-mentioned MFG-E8-L, MFG-E8-L mutant or the like which are labeled with, for instance, fluorescent materials such as FITC (Fluorescein isocyanate) or tetramethylrhodamine isocyanate, etc., radio isotopes such as $^{125}I$, $^{32}P$, $^{14}C$, $^{35}S$ or $^{3}H$, etc., or enzymes such as alkaline phosphatase, peroxidase, β-galactosidase or phycoerythrin etc., or which are bound to known peptide tags such as Myc tag, His tag, FLAG tag, GST tag and the like, or fusion proteins wherein a fluorescent protein and the like such as Green Fluorescent Protein (GFP) are fused to the MFG-E8-L, MFG-E8-L mutant or the like. Such labeling bodies can be prepared according to conventional method, and it is possible to detect a cell or tissue developing apoptosis in vivo by using such labeling bodies. Further, the above-mentioned labeled body is also useful for purification of MFG-E8-L and the like wherein the affinity of Ni-NTA and His tag is used, detection of a protein which interacts with MFG-E8-L, or as a laboratory reagent for the field of interest in addition to be detection agent for apoptotic cells/tissues.

As for the screening method for a removal promotion inducing substance or removal promotion suppressive substance for apoptotic cells in vivo by macrophages of the present invention, there is no particular limitation as long as it is a screening method wherein MFG-E8-L or MFG-E8-L mutant which has removal promotion action for apoptotic cells in vivo by macrophages, or an antibody against them is contacted with a test substance to evaluate the extent of removal of apoptotic cells in vivo. As for the screening method for a removal inhibition inducing substance or a removal inhibition suppressive substance for apoptotic cells in vivo by macrophages of the present invention, there is no particular limitation either as long as it is a screening method wherein MFG-E8-L mutant which has removal inhibition action for apoptotic cells in vivo by macrophages is contacted with a test substance to evaluate the extent of removal inhibition action for apoptotic cells in vivo, and the cells expressing the above-mentioned MFG-E8-L or MFG-E8-L mutant can be used as the MFG-E8-L or MFG-E8-L mutant and the like.

As for the above-mentioned method to evaluate the extent of removal or removal inhibition of apoptotic cells, for instance, it can be particularly exemplified by the method wherein phagocytosis of apoptotic cells by macrophages is measured and observed in vivo or in vitro in the presence of a test substance and MFG-E8-L and the like, and compared and evaluated with the case of a control in the absence of a test substance. The removal promotion inducing substance or removal inhibition suppressive substance for apoptotic cells in vivo which can be obtained by such screening method, can be possibly used as a therapeutic agent for diseases resulting from incomplete removal of apoptotic cells in vivo by macrophages or enhancer for biodefense mechanism. On the other hand, removal promotion suppressive substance or removal inhibition inducing substance can be possibly used as a therapeutic agent for diseases resulting from incomplete removal inhibition of apoptotic cells in vivo by macrophages. The removal promotion inducing substance for apoptotic cells in vivo can be exemplified by the expression system of DNA encoding integrin $\alpha_V\beta_3$ or thioglycolic acid salt, and the removal promotion suppressive substance for apoptotic cells in vivo can be exemplified by the expression system which contains whole or a part of antisense strand of DNA or RNA encoding MFG-E8-L.

The present invention will be described in detail with reference to the following examples, while the technical scope of the present invention will not be limited to these examples.

Example A

Material and Method

Example A-1

Establishment of Integrin $\alpha_V\beta_3$-expressing Mouse NIH3T3 Transformant Retrovirus carrying mouse integrin $\alpha_V$ and $\beta_3$cDNA (J. Cell Biol. 132, 1161-1176, 1996; J. Cell Biochem. 81, 320-

332, 2001) in pMX vector (Exp. Hematol. 24, 324-329, 1996) is infected with NIH3T3 cell line (ATCC CRL1658), which is a mouse fibroblast, to establish mouse NIH3T3 transformants expressing integrin $\alpha_V$ and $\beta_3$.

Example A-2

Preparation of Antibody

In order to generate a monoclonal antibody, $1.5 \times 10^7$ of thioglycollate-elicited peritoneal macrophages were subcutaneously injected into Armenian hamsters (Oriental Yeast) with 4-week intervals. The last booster was performed by injecting cells into the footpads. Cells obtained from popliteal and inguinal lymph nodes were fused with P3X63Ag8U1 mouse myeloma (ATCC CRL1597) according to ordinary protocol, and hybridomas were selected in HAT medium. The culture supernatants of hybridomas were tested by a phagocytosis assay, and positive hybridomas were cultured in GIT medium (Nihon Seiyaku), and purified with protein A-SEPHAROSE® (Amersham-Pharmacia) to obtain 2422 monoclonal antibodies.

Rabbit antibody against mouse MFG-E8 was prepared at the Peptide Institute (Minoo-shi, Osaka). In brief, m-maleimidobenzoyl-N-hydroxysuccinimide ester (Pierce) was used with a peptide bound to keyhole limpet hemocyanin (CNSHKKNIFEKPFMAR; SEQ ID NO. 3) to immunize rabbits. AF-amino-Toyopearl (Tosoh) to which the peptide is bound was used to affinity-purify the antibody from the rabbit serum.

Example A-3

Generation of Recombinant MFG-E8

Mouse MFG-E8 gene shown by SEQ ID NO. 2 was used to generate recombinant MFG-E8. MFG-E8 wherein FLAG which is a marker peptide is bound to its C-terminus was expressed in human 293T cells (ATCC CRL1573) using pEF-BOS-EX vector (Proc. Natl. Acad. Sci. USA 95, 3461-3466, 1998) according to ordinary protocol. MEG-E8 secreted into the medium was purified using anti-FLAG M2 affinity gel (Sigma). The MFG-E8-L structure includes a signal sequence, two EGF domains (EGF-1 and EGF-2 having RGD motif), a proline/threonine-rich domain (P/T-rich domain), and two factor VIII-homologous domains (C1 and C2) (FIG. 3 upper panel). Therefore, the DNA encoding the following MFG-E8-L mutant was generated by means of recombinant PCR according to the ordinary protocol, and expression plasmids were generated using the above-mentioned pEF-BOS-EX vector. By expressing these expression vectors in human 293T cells to generate the followings: "MFG-E8-S" which is a splice variant wherein P/T-rich domain is deleted; "C2 mutant" in which signal sequence is fused with C2-domain in frame; "C1C2 mutant" in which signal sequence is fused with C1-C2 domain in frame; "E1E2PT" which is an incomplete form whereon C1 and C2 domains are deleted; "D89E mutant" wherein the aspartic acid on the 89$^{th}$ position of RGD motif is substituted by glutamic acid.

Example A-4

Phagocytosis Assay

Twelve-week-old C57BL/6 mice were injected intra-peritoneally with 3% (w/v) thioglycollate (Sigma). The thioglycollate-elicited peritoneal macrophages were harvested after 4 days and cultured in DMEM containing 10% FCS. For the phagocytosis assay, thymocytes from 4-8-week-old ICAD-Sdm mice (Genes Dev. 14, 549-558, 2000) were incubated at 37° C. for 4 hours with 10 μM dexamethasone in DMEM containing 10% FCS. Thymocytes ($1 \times 10^6$ cells) were added to $2.5 \times 10^5$ macrophages grown on 48-well cell culture plates, phagocytosis was allowed to proceed for 1.5 hours. Macrophages were detached from such plates, and incubated on ice for 30 minutes in FACS staining buffer (PBS containing 2% FCS and 0.02% NaN$_3$) containing 4 μg/ml phycoerythrin-conjugated rat anti-mouse Mac-1 antibody (BD-PharMingen) in the presence of 2.5 μg/ml rat anti-mouse FcγIII/II receptors (BD PharMingen). Such cells were fixed with 1% paraformaldehyde, treated with 0.1% TRITON™ X-100, and suspended in 100 μof 100 mM cacodylate buffer (pH7.2) containing 1 mM CoCl$_2$ and 0.01% BSA. The TUNEL reaction was carried out at 37° C. for 45 minutes with 100 units/ml terminal deoxynucleotidyl transferase (Takara Shuzo) and 2.5 μM FITC-labeled dUTP (Roche Diagnositics), and analyzed by flow cytometry using a FACS caliber (Becton-Dickinson).

Phagocytosis was also evaluated by observing the cells under a microscope. In brief, peritoneal macrophages ($1 \times 10^5$ cells) or NIH3T3 cells ($2 \times 10^4$ cells) were cultured in 8-well LAB-TEK II® chamber slides (Nalge Nunc) that had been coated with 0.1% gelatin, and phagocytosis of apoptotic thymocytes was allowed to proceed as described above. After fixation, the cells were subjected to the TUNEL reaction using an APOPTAG® kit (Intergen), and observed by light microscopy.

Example A-5

Identification of MFG-E8

The 2422 monoclonal antibody was covalently linked to Protein A-SEPHAROSE® (2 mg/ml bed volume) using dimethyl pimelimidate (DMP, Pierce). Molecules recognized by 2422 monoclonal antibody were purified from mouse P388D1 cells by immunoprecipitation. In brief, $2.4 \times 10^9$ cells were lysed in RIPA buffer (50 mM Hepes-NaOH buffer [pH 7.6] containing 1% TRITON™ X-100, 0.1% SDS, 0.5% sodium deoxycholate, 150 mM NaCl, 1.5 mM MgCl$_2$, 1 mM EGTA, 10% glycerol, 1 mM [p-amidinophenyl]methanesulfonyl fluoride hydrochloride, [0039] 1 μg/ml leupeptin and 1 μg/ml pepstatin). The lysate was pretreated with 3 ml human IgG SEPHAROSE®, and incubated for hours with 150 μ2422 monoclonal antibody-Protein A-SEPHAROSE ®. After washing with RIPA buffer containing 0.5 M NaCl, proteins bound to the beads were eluted with 100 mM Triethylamine (pH 11.5) containing 0.1% TRITON® X-100, separated by electrophoresis on 10% polyacrylamide gel, and blotted onto a PVDF membrane. The immobilized protein was reduced, S-carboxymethylated, and digested with Achromobacter protease I as described previously (J. Biochem. (Tokyo) 120, 29-34, 1996).

Peptides released from the membrane were analyzed by matrix-assisted laser desorption/ionization time-of-flight (MALDI-TOF) mass spectrometry.

Example A-6

Solid-phase ELISA and Cell Adhesion Assay

The solid phase ELISA for MFG-E8 bound to phospholipids was carried out as described previously (Biochemistry 36, 5441-5446, 1997). In brief, a solution of phospholipid in methanol (3 μg/ml, 100 μl) was added to 96-well microtiter plates, and air-dried. The wells were treated with PBS containing 10 mg/ml BSA. MFG-E8 were added to the wells, and incubated at room temperature for 1 hour. After washing with PBS containing 0.05% TWEEN® 20, MFG-E 8 bound to the wells was quantified by ELISA with biotinylated anti-Flag antibody and peroxidase-conjugated streptavidin. Peroxidase activity was detected using a peroxidase-detecting kit (Sumitomo Bakelite). To assay the ability of MFG-E8 to link the cells to phospholipids, MFG-E8 was bound to microtiter plates coated with phospholipids as described above. In tyrode buffer containing the cells ($4 \times 10^4$) (5 mM Hepes-NaOH buffer [pH 7.4], 135 mM NaCl, 5.4 mM KCl, 1.0 mM $MgCl_2$, 10 mM glucose, and 10 mg/ml BSA) was added to each well, and incubated at room temperature for 1 hour. The cells that had adhered to the plates were quantified by a CYQUANT® Cell Proliferation Assay kit (Molecular Probes) using a fluorescent microplate reader (BioLumin 960, Molecular Dynamics) set at excitation wavelength of 485 nm and emission wavelength of 520 nm.

Example B

Results

Example B-1

Establishment of Monoclonal Antibody that Enhances the Phagocytosis of Apoptotic Cells The cells expressing a caspase resistant-mutant of ICAD which is a inhibitor protein of caspase activated DNase(CAD) do not undergo apoptotic DNA fragmentation, but their DNA can still be cleaved when the cells are engulfed by macrophages (Genes Dev. 14, 549-558, 2000). This system was used to examine the phagocytosis of apoptotic cells by macrophages. Thymocytes from ICAD-Sdm (a short-stranded caspase resistant ICAD) mice were untreated or treated with dexamethasone for 4 hours, and stained with phycoerythrin-conjugated Annexin V (BD PharMingen) or TUNEL using FITC-conjugated dUTP. As shown in FIG. 1a, when the thymocytes from ICAD-Sdm mice were treated with dexamethasone, approximately 50% of the cells turned Annexin V-positive within 4 hours, however, they were not stained by TUNEL.

In the next place, the thioglycollate-elicited mouse peritoneal macrophages were incubated with freshly prepared or dexamethasone-treated thymocytes from ICAD-Sdm mice. The cells were stained with phycoerythrin-conjugated anti-Mac-1 antibody, followed by TUNEL staining with FITC-dUTP. When the macrophages were cocultured with ICAD-Sdm thymocytes in the presence of apoptotic cells instead of freshly prepared thymocytes, approximately 40% of the Mac-1$^+$ cells (cell surface antigen Mac-1-expressing cells of macrophage-like cell line) turned TUNEL-positive (FIG. 1b lower part). Bafilomycin (100 nM) was added to macrophages 30 minutes before the incubation with the dexamethasone-treated thymocytes. Thus, when the macrophages are treated with bafilomycin which prevents oxidization of lisosome (Proc. Natl. Acad. Sci. USA 85, 7972-7976, 1988), the emergence of TUNEL-positive macrophages was inhibited. The upper panels of FIG. 1b show the TUNEL-staining profiles in the Mac-1$^+$ population. These results suggest that such macrophages incorporate apoptotic cells specifically, and they digest their chromosomal DNA.

Figure 1C:
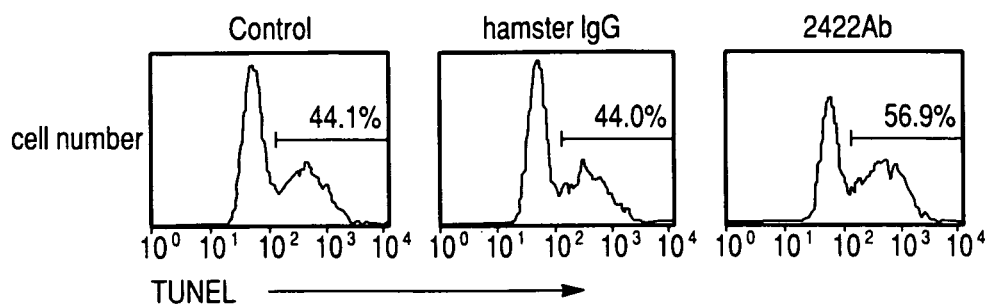
Figure 1D:
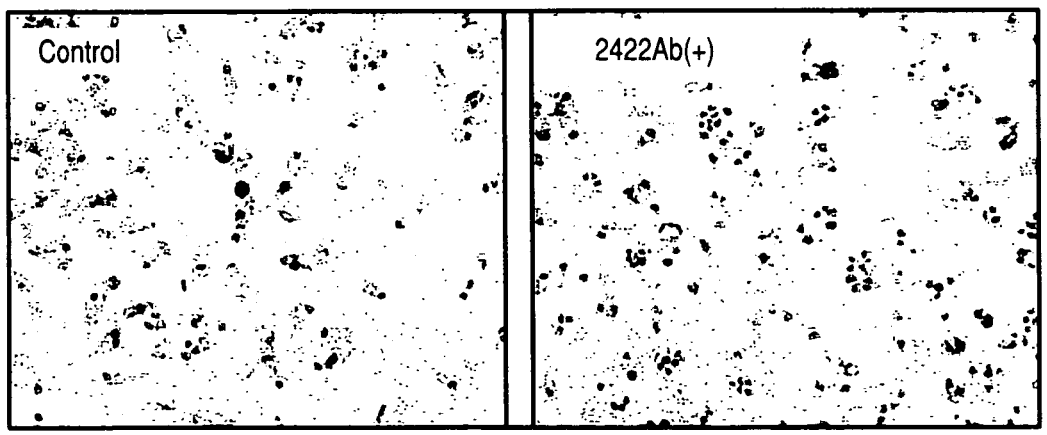

In order to identify mediators of this process, the thioglycollate-elicited mouse peritoneal macrophages were used to immunize Armenian hamsters, and hybridomas were prepared. It was found that particular antibody (2422 monoclonal antibody) promotes the phagocytosis. In brief, phagocytosis was assayed in the absence, or presence of 12 μg/ml normal hamster IgG, or 2422 monoclonal antibody. The FACS profiles of TUNEL-staining in the Mac-1$^+$ population are shown in FIG. 1c. The numbers indicate the percentage of TUNEL-positive cells in the Mac-1$^+$ population. These results showed that the percentage of macrophages which engulf apoptotic cells increased from 44% to 57% in the presence of 2422 monoclonal antibody. As a result of observation under a light microscopy (×400), it was found that not only the number of macrophages which engulf apoptotic cells, but also the number of apoptotic cells engulfed by one macrophage increases in the presence of 2422 monoclonal antibody, as shown in FIG. 1d.

Example B-2

Identification of 2422 Monoclonal Antibody-recognition-protein

Figure 2A:
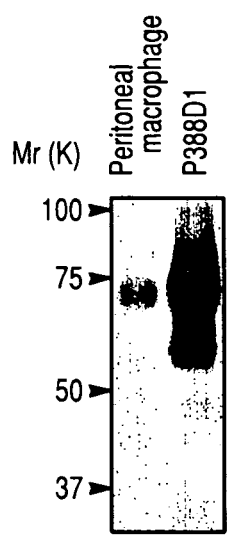
FIG. 2a is a photograph showing the results of immunoprecipitation using 2422 monoclonal antibody, of thioglycollate-elicited peritoneal macrophages and the macrophage cell line P388D1 that have been surface-labeled with biotin.
Figure 2B:
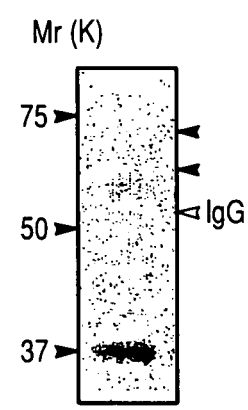
FIG. 2b is a photograph showing the results of Ponceau-S staining of protein obtained by subjecting P388D1 cell lysates to affinity-purification using 2422 monoclonal antibody, then to separation by electrophoresis on a polyacrylamide gel, which was then transferred to a PVDF membrane.

In order to identify proteins recognized by 2422 monoclonal antibody, the thioglycollate-elicited peritoneal macrophages or the macrophage cell line P388D1 were surface-labeled with biotin, and proteins recognized by 2422 monoclonal antibody was immunoprecipitated. As a result of Western blotting with streptavidin-peroxidase for an immune precipitate, the bands of 72 kDa and 56 kDa appeared as shown in FIG. 2a. As shown in FIG. 2a, since P388D1 cell lines express proteins more abundantly than did peritoneal macrophages, P388D1 cells were cultured on a large scale, and proteins recognized by 2422 monoclonal antibody were affinity-purified from cell lysates using such antibody, separated by electrophoresis on a polyacrylamide gel, transferred to a PVDF membrane, and stained with Ponceau-S. The results are shown in FIG. 2b. The arrows in FIG. 2b indicate proteins subjected to protein sequence analysis, and IgG released from protein A SEPHAROSE®. As a result of mass spectrometry of peptides generated from the proteins of 72 kDa and 56 kDa, it was found that they are mouse MFG-E8 (Proc. Natl. Acad. Sci. USA 87, 8417-8421, 1990; Biochem. Biophys. Res. Commun. 254. 522-528, 1999).

Figure 2C:
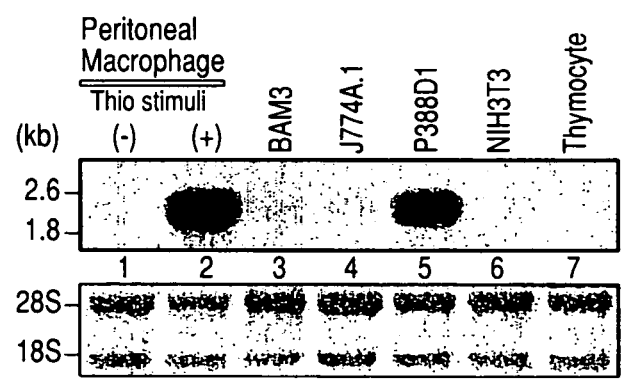
FIG. 2c is a photograph showing the results of Northern hybridization using $^{32}$P-labeled murine MFG-E8 cDNA, which detected MFG-E8-L and MFG-E8-S expressions on thioglycollate-elicited peritoneal macrophages and P388D1 cells.

Two classes of cDNA (MFG-E8-L and MFG-E8-S) were isolated from mouse peritoneal macrophages by reverse transcription-polymerase chain reaction (RT-PCR) using the primer having mouse MFG-E8 sequence. In the next place, total RNA (7.5 μg) derived from thioglycollate-elicited peritoneal macrophages and P388D1 cells were separated by electrophoresis on a 1.5% agarose gel and analyzed by Northern hybridization using $^{32}$P-labeled murine MFG-E8 cDNA (FIG. 2c upper panel; in FIG. 2c lower panel, the filter was stained with 0.05% (w/v) methylene blue). Northern blotting showed that MFG-E8 mRNA was abundantly expressed in thioglycollate-elicited peritoneal macrophages and P388D1 cells. In contrast, little MFG-E8 mRNA was detected in peritoneal macrophages and thymocytes in the resting period. Several other macrophage cell lines such as J774A.1 and BAM3 and the like, and the fibroblast cell line NIH3T3 expressed little MFG-E8 mRNA (FIG. 2c).

Figure 2D:
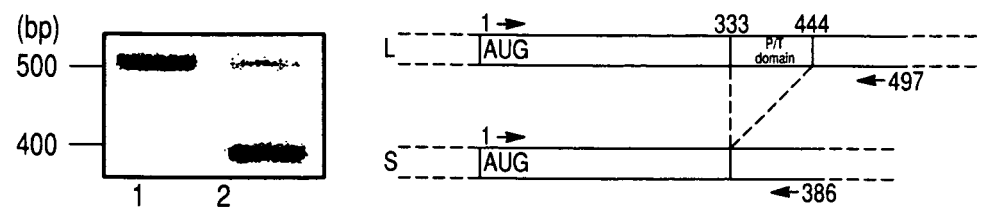
FIG. 2d is a photograph showing the results of examining MFG-E8-L and MFG-E8-S expressions on thioglycollate-elicited peritoneal macrophages and P388D1 cells by performing RT-PCR using primers shown in SEQ ID NOs: 4 and 5.
Figure 2E:
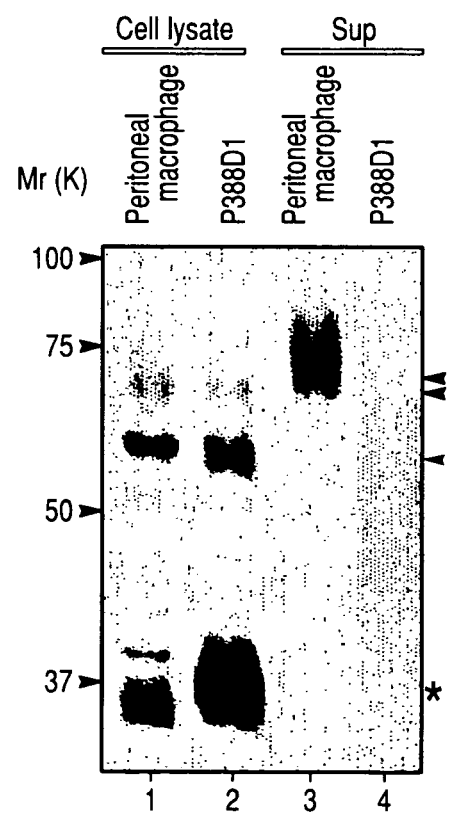
FIG. 2e is a photograph showing the results of Western blotting with rabbit anti-MFG-E8 antibodies after the cell lysates and culture supernatants of thioglycollate-elicited peritoneal macrophages and P388D1 cells were subjected to immunoprecipitation with 2422 monoclonal antibody.

Total RNA (0.3 μg) from thioglycollate-elicited peritoneal macrophages and P388D1 were analyzed by RT-PCR. A portion of the MFG-E8 mRNA is shown schematically in the right panel of FIG. 2d. Primers used are indicated by arrows: the sense primer, ATGCAGGTCTCCCGTGTGCT (SEQ ID NO.4: P1) and the anti-sense primer, GCGGAAATCTGT-GAATCAGC (SEQ ID NO 5: P2). The PCR products were separated by electrophoresis on an agarose gel. RT-PCR analysis showed that P388D1 cells dominantly express short strand (MFG-E8-S) as opposed to that MFG-E8 mRNA in the thioglycollate-elicited peritoneal macrophages mainly encodes long strand (MFG-E8-L). Therefore, the thioglycollate-elicited peritoneal macrophages and P388D1 were cultured for 48 hours. The cell lysates and culture supernatants were immunoprecipitated with 2422 monoclonal antibody, and subjected to Western blotting with rabbit anti-MFG-E8 antibodies. The results are shown in FIG. 2e. MFG-E8 proteins are indicated by arrows at the right in FIG. 2e. It is suggested that MFG-E8 is a secretory protein since it has no putative transmembrane region though it has a signal sequence at the N-terminus. As shown in these results, the culture supernatant of thioglycollate-elicited peritoneal macrophages contained a large amount of MFG-E8 of 74 kDa. On the other hand, P388D1 cells secreted negligible levels of MFG-E8, although the cell lysates contained a substantial amount of MFG-E8. It suggests that MFG-E8 expressed in P388D1 cells is not sufficiently secreted. Bands indicated by * in FIG. 2e are probably degraded products of MFG-E8.

Example B-3

Binding of MFG-E8 to Aminophospholipids Exposed on Apoptotic Cells

Figure 3A:
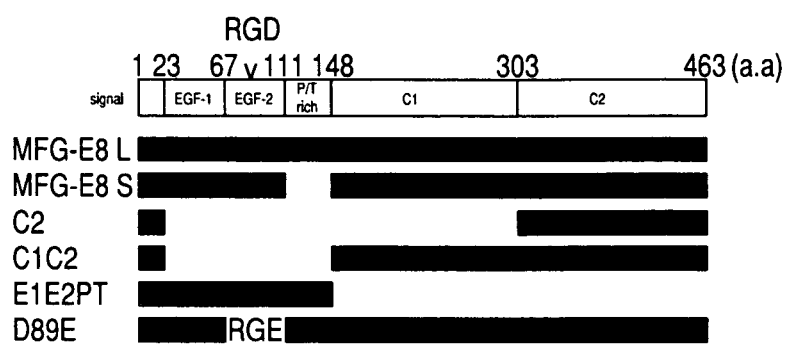
FIG. 3a shows the FLAG-conjugated recombinant MFG-E8-L generated in Example of the present invention.
Figure 3B:
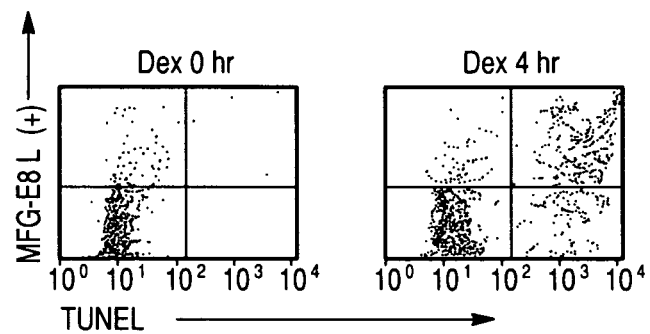
FIG. 3b shows the results of TUNEL staining of freshly prepared wild-type thymocytes or dexamethasone-treated thymocytes, after the thymocytes were incubated with MFG-E8-L.

In order to examine whether MFG-E8 binds to apoptotic cells, FLAG-conjugated recombinant MFG-E8-L (FIG. 3a) was generated in human 293T cells, purified to homogeneity. Freshly prepared wild-type thymocytes ($5 \times 10^5$ cells) or thymocytes treated with dexamethasone for 4 hours were incubated at 4° C. for 30 minutes with 0.25 µg/ml FLAG-conjugated MFG-E8-L, followed by double-staining with biotinylated anti-FLAG antibody, and phycoerythrin-conjugated streptavidin. After fixation, the cells were subjected to TUNEL staining with FITC-dUTP, and analyzed by FACS. The results are shown in FIG. 3b. As shown in FIG. 3b, MFG-E8-L does not bind to freshly isolated thymocytes, but tightly bound to the thymocytes treated with dexamethasone. If such thymocytes treated with dexamethasone are double stained with MFG-E8-L and TUNEL, it can be found that MFG-E8-L specifically binds to the TUNEL-positive apoptotic cells.

Figure 3C:
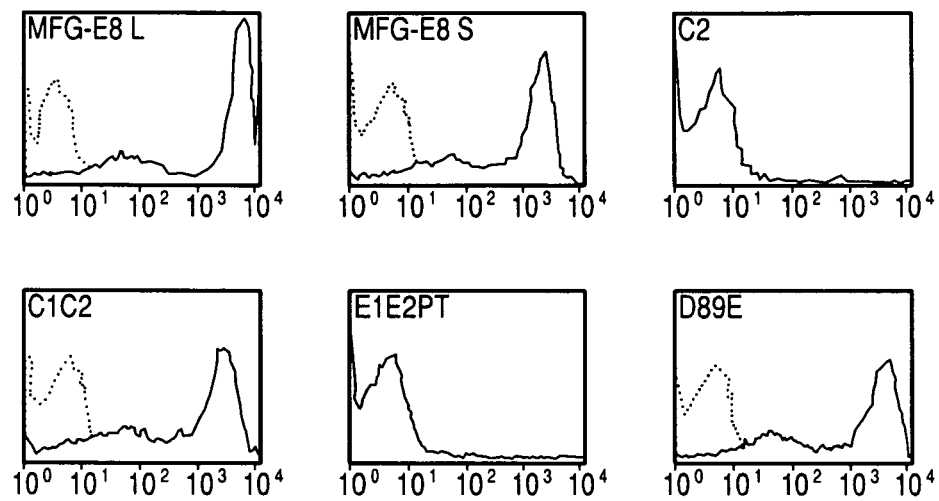
FIG. 3c shows the results of FACS analysis using FITC-labeled anti-FLAG antibody on dexamethasone-treated thymocytes, after the thymocytes were incubated with various MFG-E8 derivatives.

As mentioned above, MFG-E8-L contains a signal sequence, two EGF domains, a proline/threonine-rich domain (P/T-rich domain), and two factor VIII-homologous domains (C1 and C2). MFG-E8-S is encoded by MFG-E8 mRNA spliced in various forms and its P/T-rich domain is deleted. In order to study which domain of MFG-E8-L is involved in binding to apoptotic cells, examination was carried out using MFG-E8-S and a series of MFG-E8-L mutants. Thymocytes were treated with dexamethasone for 6 hours, and incubated with 0.25 µg/ml of various MFG-E8 derivatives. MFG-E8 bound to thymocytes was analyzed by FACS analysis using FITC-labeled anti-FLAG antibody. The results are shown in FIG. 3c. Dotted lines in FIG. 3c show the staining profiles in the absence of MFG-E8. As shown in FIG. 3c, MFG-E8-S, D89E having point mutation in RGD motif, C1C2 containing C1 domain and C2 domain only, as well as MFG-E8-L bound to thymocytes in the presence of apoptotic cells.

Figure 3D:
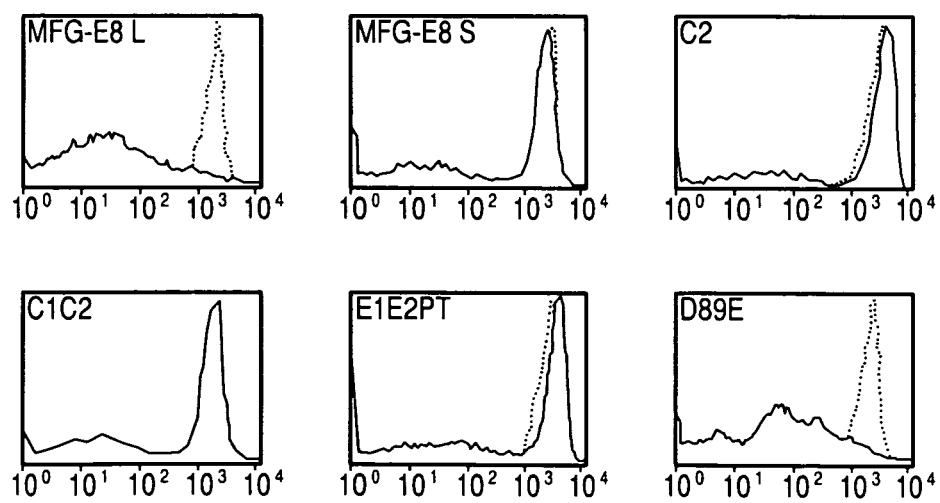
FIG. 3d shows the results of FACS analysis using phycoerythrine-conjugated annexin V on dexamethasone-treated thymocytes, after the thymocytes were incubated with various MFG-E8 derivatives.

In the meantime, it is known that Annexin V binds to apoptotic cells by recognizing phosphatidylseline (PS) (Blood 84, 1415-1420, 1994). Therefore, thymocytes treated with dexamethasone for 6 hours were incubated with 1.25 µg/ml MFG-E8-L or various mutants, and stained with phycoerythrine-conjugated annexin V. The results are shown in FIG. 3d. Annexin V-staining profile in the absence of MFG-E8 is shown by dotted lines in FIG. 3d. As shown in FIG. 3d, when thymocytes in the presence of apoptotic cells are pretreated with MFG-E8-L or D89E, binding of Annexin V to apoptotic cells was largely inhibited. Further, inhibition effect of MFG-E8-L on binding of Annexin V was dose-dependent, and when treated with 0.25 µg/ml of MFG-E8-L, 50% of binding of Annexin V was inhibited. On the other hand, binding of Annexin V to apoptotic cells was not inhibited by the presence of MFG-E8-S or C1C2. This shows that affinity of MFG-E8-S for apoptotic cells is considerably lower than that of MFG-E8-L.

Figure 3E:
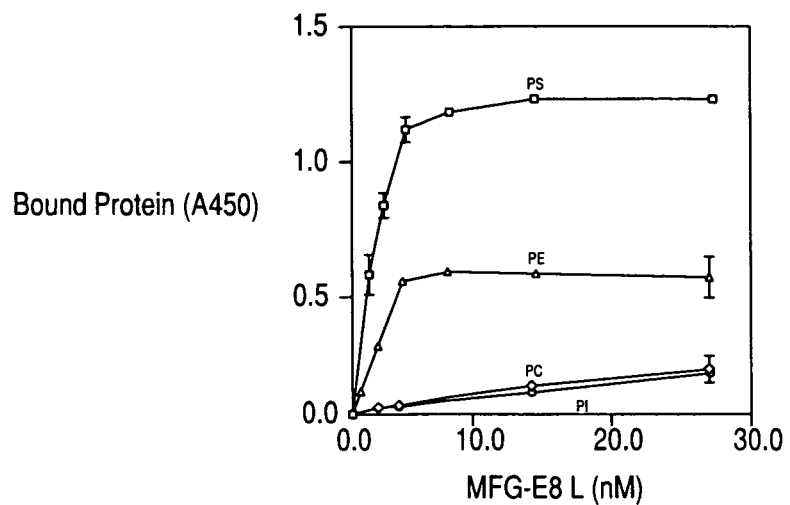
FIG. 3e shows the results of quantification of MFG-E8-L bound to the wells by ELISA after microtiter plates coated with phosphatidylserine (PS), phosphatidylethanolamine (PE), phosphatidylcholine (PC), or phosphatidylinositol(PI) were incubated with increasing concentrations of MFG-E8-L.

Antagonistic action of MFG-E8-L for binding of Annexin V to apoptotic cells suggested that MFG-E8-L was bound to PS. Therefore, bindings of MFG-E8-L to various phospholipids were investigated. Microtiter plates coated with phosphatidylserine (PS), phosphatidylethanolamine (PE), phosphatidylcholine (PC), or phosphatidylinositol(PI) were incubated with increasing concentrations of MFG-E8-L. MFG-E8-L bound to the wells was quantified by ELISA using the anti-FLAG antibody. The results are shown in FIG. 3e. As shown in FIG. 3e, although MFG-E8-L bound to the plates coated with PS or PE in a saturating manner, MFG-E8-L did not significantly bind to the plates coated with PC or PI.

In the next place, binding to phosphatidylseline was also examined for D89E mutant which is a point mutant derivative of MFG-E8-L which has antagonistic activity for binding of Annexin V for apoptotic cells in the same manner as for MFG-E8-L. Microtiterplates coated with PS were incubated with increasing concentrations of MFG-E8-L, MFG-E8-S, or C1C2 mutant as well as D89E, and MFG-E8 bound to the wells was quantified by ELISA.

Figure 3F:
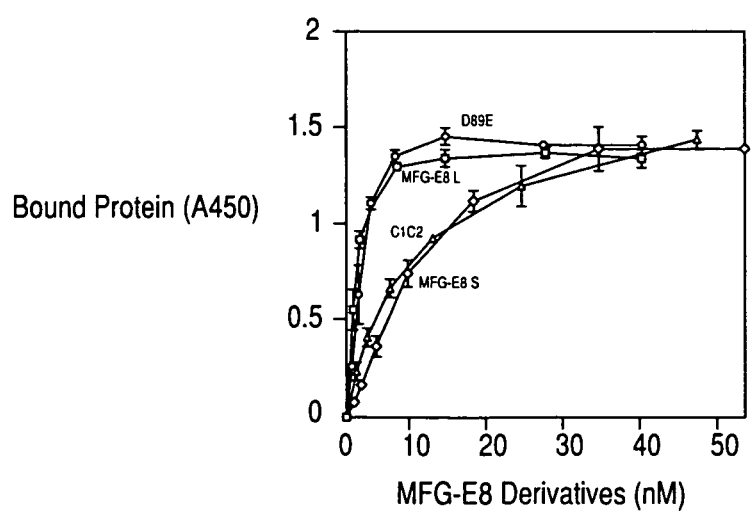
FIG. 3f shows the results of quantification of MFG-E8-L bound to the wells by ELISA after microtiter plates coated with PS were incubated with increasing concentrations of MFG-E8-L, MFG-E8-S, or C1C2mutant as well as D89E.

The results are shown in FIG. 3f. As shown in FIG. 3f, D89E mutants of MFG-E8-L bound to the plates coated with PS as efficiently as did the wild-type MFG-E8-L. However, the affinity of MFG-E8-S and C1C2 mutant for the plates coated with PS was one-eighth of the affinity of MFG-E8-L. These results showed that MFG-E8-L is capable of recognizing aminophopholipid via its C1C2 domain, and that P/T-rich domain present in MFG-E8-L is involved in the affinity of MFG-E8-L against such phospholipids.

Example B-4

Binding of NIH3T3 Cells to Aminophospholipids Via MFG-E8

Figure 4A:
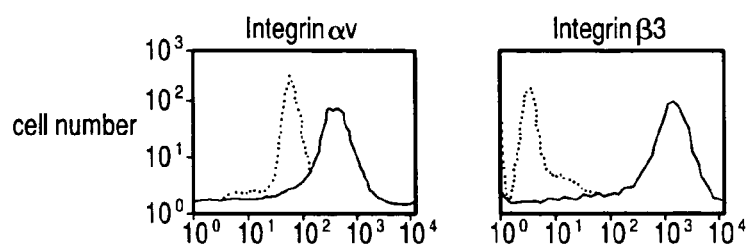
FIG. 4a shows the results of FACS analysis on NIH3T3 transformants expressing the mouse $\alpha_v\beta_3$ integrin, using phycoerythrine-conjugated hamster anti-mouse integrin $\alpha_v$ or integrin $\beta_3$ antibodies.

In the second EGF domain of MFG-E8, RGD motif which can be recognized by some members of integrin family which is a cell transmembrane receptor involved in cell adhesion (Cell 69, 11-25, 1992). Therefore, the possibility that MFG-E8-L acts as a bridge between apoptotic cells expressing aminophospholipids and phagocytes expressing integrins was considered. The NIH3T3 transformants expressing the mouse $\alpha_V \beta_3$ integrin were analyzed by FACS using phycoerythrine-conjugated hamster anti-mouse integrin $\alpha_V$ or integrin $\beta_3$ antibodies. The results are shown in FIG. 4a. The FACS staining profile for the parental NIH3T3 cell is shown by dotted lines in FIG. 4a. As shown in FIG. 4a, although mouse NIH3T3 parent cells express $\alpha_V$ and $\beta_3$ integrins at low level, when this parent cell line is transformed with $\alpha_V$ and $\beta_3$ integrin-expressing vectors it abundantly expressed both $\alpha_V$ and $\beta_3$ integrins.

Figure 4B:
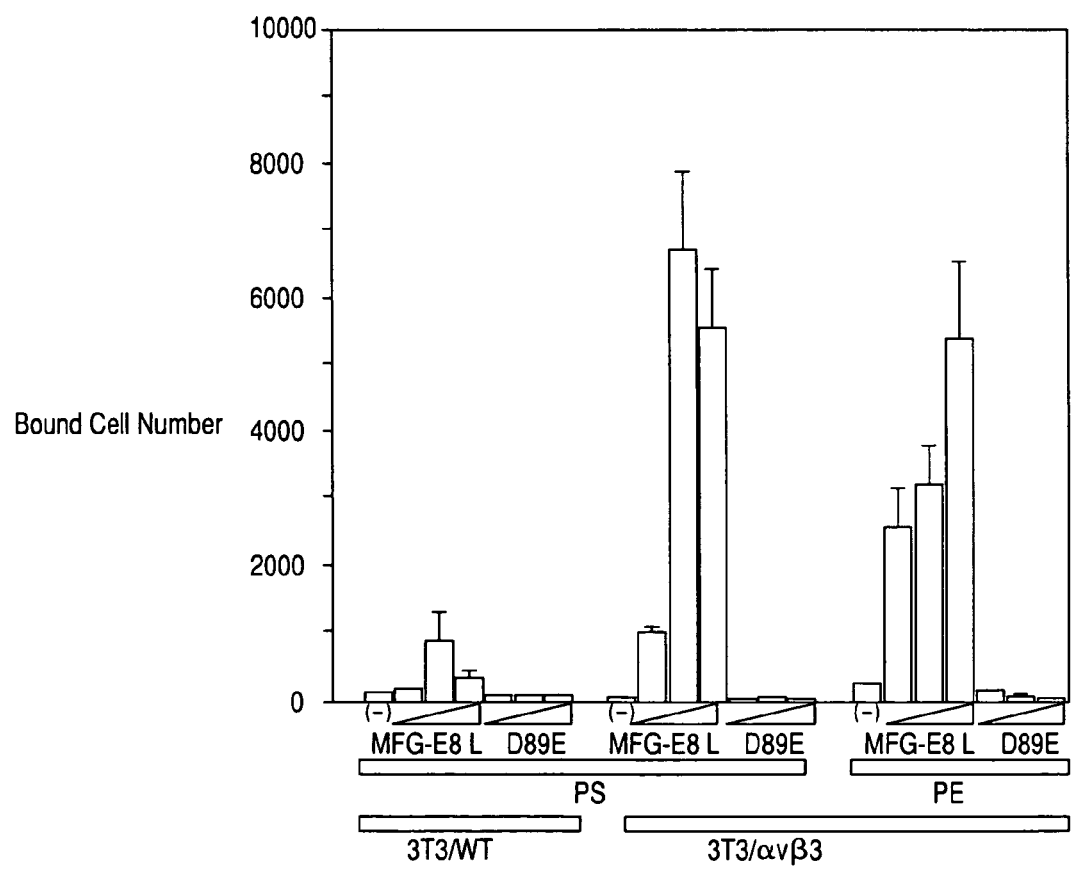
FIG. 4b shows the results of cell adhesion assay using microtiter wells coated with PS or PE, to examine the adhesion of NIH3T3 (3T3/WT) or its transformant expressing $\alpha_v\beta_3$ integrin (3T3/$\alpha_v\beta_3$) to three different concentrations (0.1, 1.0 and 2.0 μg/ml) of MFG-E8-L or D89E.

FACS analysis using FLAG-conjugated MFG-E8 did not show specific binding between MFG-E8L and NIH3T3 or its $\alpha_V \beta_3$ integrin transformant. Therefore, the possibility that MFG-E8-L might bind to integrin-expressing cells after said cells are bound to phospholipids was investigated. Microtiter wells coated with PS or PE were successively incubated with three different concentrations (0.1, 1.0 and 2.0 µg/ml) of MFG-E8-L or D89E, and with NIH3T3 (3T3/WT) or $\alpha_v\beta_3$ integrin-expressing transformants (3T3/$\alpha_v\beta_3$) and subjected to cell adhesion assay. The number of cells attached to the wells was quantified as described in the methods described in Example A-6. The results are shown in FIG. 4b. As shown in FIG. 4b, NIH3T3 parent cells (3T3/WT) did not bind to the plates coated with PS in the absence of MFG-E8-L. On the other hand, when the plates coated with PS were preincubated in the presence of MFG-E8-L, considerable amount of NIH3T3 cells adhered to the wells. D89E mutant was not capable of intermediating the adhering of NIH3T3 cells to the wells coated with PS. It shows that the effect of such MFG-E8-L is caused by its RGD motif. When NIH3T3 cells (3T3/$\alpha_v\beta_3$) expressing $\alpha_v\beta_3$ integrin were used as a target, activity of MFG-E8-L against cell adhesion to the wells coated with PS was more drastic. In brief, approximately 7000 cells were adhered to the wells pretreated with 1.0 µg/ml MFG-E8-L, as opposed to only 20 cells were adhered to the wells untreated or treated with D89E. Binding ability of MFG-E8-L to PE was in similar efficiency as with the wells coated with PS, and the wells coated with PE also supported the adhesion of NIH3T3 cell transformant.

Example B-5

MFG-E8-L Dependent Incorporation of Apoptotic Cells

In the next place, it was investigated whether it is possible for MFG-E8-L to stimulate NIH3T3 cells to engulf apoptotic cells. NIH3T3 (3T3/WT) or its transformant expressing $\alpha_v\beta_3$ integrin (3T3/$\alpha_v\beta_3$) was incubated in the absence (-) or presence of 0.1 µg/ml of MFG-E8-L, MFG-E8-S, or D89E with freshly prepared thymocytes from ICAD-Sdm mice (Dex(-)) or with tymocytes that had been treated for 4 hours with dexamethasone (Dex (+)). The number of NIH3T3 cells that engulfed more than 3 thymocytes was counted, and the percentage of these cells to the total number of NIH3T3 cells (150 cells) was determined. The experiments were performed at least twice in triplicate, and the average number is shown by SD (bars)) in FIG. 5a. As shown in FIG. 5a, when thymocytes freshly prepared from ICAD-Sdm mice were cocultured with NIH3T3 cells for two hours, there was no thymocyte which was adhered or engulfed by NIH3T3 cells in the absence or presence of MFG-E8-L, however, when the thymocytes treated with dexamethasone were cocultured with NIH3T3 cells, approximately 6% of NIH3T3 cells engulfed more than 3 thymocytes. Besides, the presence of MFG-E8-L increased the ratio of NIH3T3 cells which engulfed more than three thymocytes to 23%.

Figure 5B:
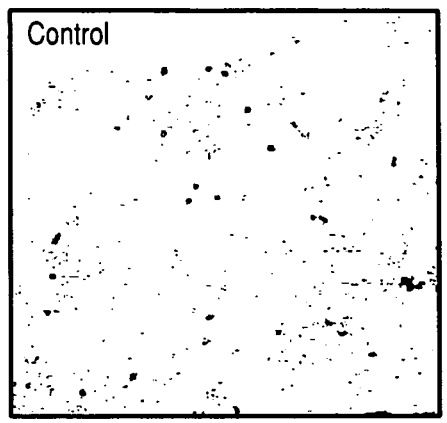
FIG. 5b is a photograph showing the results of light-microscopic observation of NIH3T3 cell transformants expressing $\alpha_v\beta_3$ integrin incubated with apoptotic thymocytes in the absence (control) or presence of MFG-E8-L or D89E.
Figure 5B:
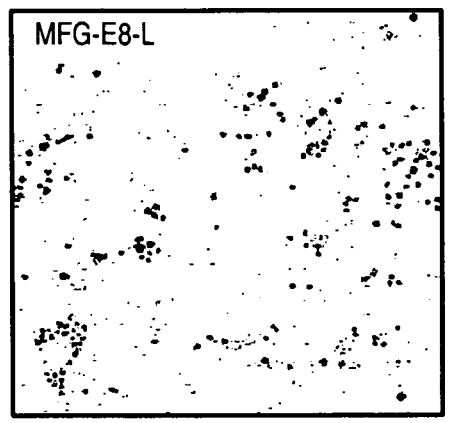
Figure 5B:
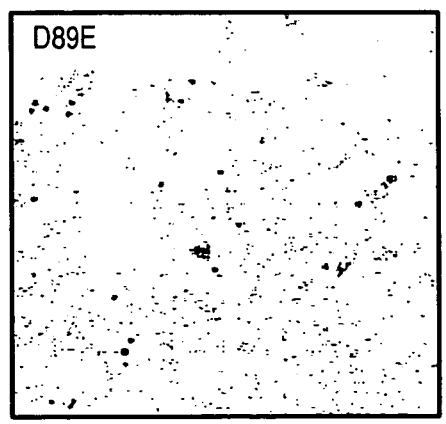

In the next place, the NIH3T3 cell transformants expressing $\alpha_v\beta_3$ integrin were incubated with apoptotic thymocytes in the absence (control) or presence of MFG-E8-L or D89E, and were observed under a light microscopy (×200). The results are shown in FIG. 5b. As shown in FIG. 5b, the influence of MFG-E8-L on phagocytosis was more clear when NIH3T3 transformant which expresses $\alpha_v\beta_3$ integrin was used as a phagocyte. In this case, the percentage of NIH3T3 transformant which engulfed more than 3 thymocytes was increased from 9% to 46% if MFG-E-L is added to the analysis mixture, and approximately 20% of the cells engulfed more than 6 thymocytes. The effect of MFG-E8-S or D89E for phagocytosis of NIH3T3 cells was rarely seen.

NIH3T3 cell transformants expressing $\alpha_v\beta_3$ integrin were cocultured with apoptotic thymocytes in the presence of increasing concentrations of MFG-E8-L or D89E, and the percentage of cells that engulfed more than 3 thymocytes was determined. The average number obtained from two experiments performed in triplicate is plotted with SD (bars) in FIG. 5c. The result shown in FIG. 5c wherein MFG-E8-L was used with various concentrations showed that optimal concentration of MFG-E8-L for increasing phagocytosis existed. With equal to or less than 0.1 µg/ml, MFG-E8-L enhance the phagocytosis in a dose-dependent manner, however, with higher concentration, inhibitory effect appeared. This inhibitory activity disappeared by adding 2422 monoclonal antibody.

Figure 5C:
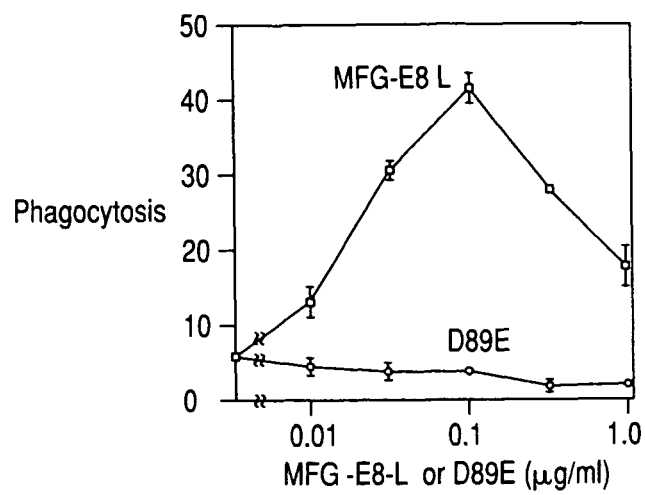
FIG. 5c shows the results of determining percentage of cells that engulfed more than 3 thymocytes, after NIH3T3 cell transformants expressing $\alpha_v\beta_3$ integrin were cocultured with apoptotic thymocytes in the presence of increasing concentrations of MFG-E8-L or D89E.
Figure 5D:
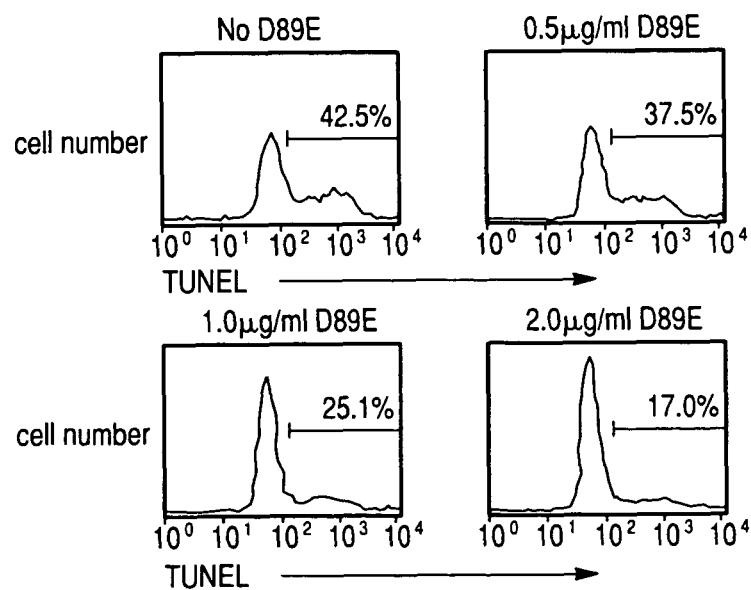
FIG. 5d shows the results of TUNEL staining of dexamethasone-treated thymocytes that have been cocultured with thioglycollate-elicited peritoneal macrophages in the presence of different concentrations of D89E.

On the other hand, unlike wild-type MFG-E8-L, D89E mutant inhibit the phagocytosis of NIH3T3 cells or their transformant in a large range of concentration (FIGS. 5a and 5c). Using this characteristics of D89E, the involvement of MFG-E8-L to phagocytosis of apoptotic cells by peritoneal macrophages was evaluated. Thymocytes from ICAD-Sdm mice were treated with dexamethasone for 4 hours, and cocultured with thioglycollate-elicited peritoneal macrophages in the presence of the indicated concentrations of D89E shown in FIG. 5d. After the reaction, the cells were stained with Phycoerythrine-conjugated anti-Mac-1 antibody, and TUNEL was carried out with FITC-dUTP. The FACS profile for TUNEL-positive cells in the Mac-1$^+$ cell population is shown in FIG. 5d. The numbers in FIG. 5d indicate the percentage of TUNEL-positive macrophages obtained in two independent assays. As shown in FIG. 5d, when thioglycollate-elicited peritoneal macrophages were cocultured with thymocytes derived from ICAD-Sdm mouse treated with dexamethasone, approximately 42% of macrophages turned TUNEL-positive. The emergence of TUNEL-positive cells and phagocytosis of thymocytes by macrophages were largely inhibited by D89E in a dose-dependent manner. This showed that MFG-E8-L expressed in macrophages played an important role in phagocytosis of apoptotic cells.

Example C

Conclusion

Many proteins expressed in phagocytes are reported as receptors involved in engulfment of apoptotic cells (Trends Cell Biol. 8, 365-372, 1998; Cell Death Differ. 5. 551-562, 1998; Nature 407, 784-788, 2000). However, it was not clear whether these receptors directly bind to apoptotic cells. The present inventors showed herein that MFG-E8-L specifically bound to apoptotic cells by recognizing aminophospholipids such as PS, PE and the like. Aminophospholipids localized to the inner leaflet of the plasma membrane in proliferating or resting period exposed on the cell surface when the cells are triggered to undergo apoptosis (J. Immunol. 149, 4029-4035, 1992; Exp. Cell Res. 232, 430-434, 1997; Proc. Natl. Acad. Sci. USA 95, 6349-6354, 1998). The cells which are made to express PS using liposome transfer method are recognized and engulfed by phagocytes (J. Biol. Chem. 270. 1071-1077, 2001). These facts show that exposed PS fulfills the criteria for an "eat me" signal. Most of the molecules reported as receptors for apoptotic cells bind not only to PS but also to PI (Cell Death Differ. 5, 551-562, 1998; J. Biol. Chem. 276, 16221-16224, 1995). On the other hand, MFG-E8-L exclusively binds to PS and PE, supporting the idea that MFG-E8-L specifically recognize apoptotic cells.

Integrins have been suggested as a receptor for apoptotic cells in several systems (Nature 343, 170-173, 1990; Nature 392, 86-89, 1998). However, it has not been clear how these integrins recognize apoptotic cells since neither $\alpha_v\beta_3$ nor $\alpha_v\beta_5$ integrins can bind to PS. It is considered that this dilemma will be solved by MFG-E8-L, and integrin can be acknowledged as a receptor for apoptotic cells in thioglycollate-elicited peritoneal macrophages. Whether other phagocytes use this system, or other systems such as PSR (Nature 405, 85-90, 2000) or MER (Nature 411, 207-211, 2001) remains to be studied.

MFG-E8 was originally identified as one of the most abundant proteins in the membranes of milk fat globules (Proc. Natl. Acad. Sci. USA 87, 8417-8421, 1990). Mammary gland undergo massive involution when suckling and milking ceases (J. Mammary Gland Biol. Neoplasia 4, 129-136, 1999) . During this process, a large number of epithelial cells are killed by apoptotic cells. It is further necessary to remove those apoptotic cells by infiltrating macrophages or viable epithelial cells, to insure the remodeling of the mammary gland in preparation for the next wave of lactation (J. Mammary Gland Biol. Neoplasia 4, 203-211, 1999). Identification of MFG-E8-L as a molecule that recognizes the apoptotic cells would help to elucidate the molecular mechanism behind involution and remodeling of mammary gland at the end of lactation.

INDUSTRIAL APPLICABILITY

According to the present invention, it is possible to provide a removal promoter which is capable of rapidly removing apoptotic cells in vivo by macrophages, or a removal inhibitor which is capable of inhibiting the removal of apoptotic cells in vivo by macrophages.

What is claimed:

1. A method for promoting phagocytosis of apoptotic cells by macrophages, comprising contacting said apoptotic cells and said macrophages with a composition comprising isolated human milk fat globule-EGF factor 8-L (MFG-E8-L).

2. The method according to claim 1, wherein the human MFG-E8-L is a translation product in human cells.

3. The method according to claim 1, wherein the human MFG-E8-L is enveloped or embedded in liposome.

* * * * *

SEQUENCE LISTING

```
<160> NUMBER OF SEQ ID NOS: 5

<210> SEQ ID NO 1
<211> LENGTH: 463
<212> TYPE: PRT
<213> ORGANISM: Mus musculus

<400> SEQUENCE: 1

Met Gln Val Ser Arg Val Leu Ala Ala Leu Cys Gly Met Leu Leu Cys
 1               5                  10                  15

Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
            35                  40                  45

Cys Leu Cys Pro Glu Gly Phe Thr Gly Leu Val Cys Asn Glu Thr Glu
        50                  55                  60

Arg Gly Pro Cys Ser Pro Asn Pro Cys Tyr Asn Asp Ala Lys Cys Leu
 65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
    130                 135                 140

Ala Ser Arg Cys Ser Thr Gln Leu Gly Met Glu Gly Gly Ala Ile Ala
145                 150                 155                 160

Asp Ser Gln Ile Ser Ala Ser Ser Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp Thr Ala Ser Asn Tyr Asp Ser Lys Pro Trp Ile Gln Val
        195                 200                 205

Asn Leu Leu Arg Lys Met Arg Val Ser Gly Val Met Thr Gln Gly Ala
    210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
                245                 250                 255
```

```
Asp Lys Glu Phe Leu Gly Asn Leu Asp Asn Asn Ser Leu Lys Val Asn
            260                 265                 270
Met Phe Asn Pro Thr Leu Glu Ala Gln Tyr Ile Arg Leu Tyr Pro Val
        275                 280                 285
Ser Cys His Arg Gly Cys Thr Leu Arg Phe Glu Leu Leu Gly Cys Glu
    290                 295                 300
Leu His Gly Cys Ser Glu Pro Leu Gly Leu Lys Asn Asn Thr Ile Pro
305                 310                 315                 320
Asp Ser Gln Met Ser Ala Ser Ser Tyr Lys Thr Trp Asn Leu Arg
            325                 330                 335
Ala Phe Gly Trp Tyr Pro His Leu Gly Arg Leu Asp Asn Gln Gly Lys
        340                 345                 350
Ile Asn Ala Trp Thr Ala Gln Ser Asn Ser Ala Lys Glu Trp Leu Gln
    355                 360                 365
Val Asp Leu Gly Thr Gln Arg Gln Val Thr Gly Ile Ile Thr Gln Gly
370                 375                 380
Ala Arg Asp Phe Gly His Ile Gln Tyr Val Ala Ser Tyr Lys Val Ala
385                 390                 395                 400
His Ser Asp Asp Gly Val Gln Trp Thr Val Tyr Glu Glu Gln Gly Ser
            405                 410                 415
Ser Lys Val Phe Gln Gly Asn Leu Asp Asn Asn Ser His Lys Lys Asn
        420                 425                 430
Ile Phe Glu Lys Pro Phe Met Ala Arg Tyr Val Arg Val Leu Pro Val
    435                 440                 445
Ser Trp His Asn Arg Ile Thr Leu Arg Leu Glu Leu Leu Gly Cys
450                 455                 460

<210> SEQ ID NO 2
<211> LENGTH: 1392
<212> TYPE: DNA
<213> ORGANISM: Mus musculus

<400> SEQUENCE: 2
atgcaggtct cccgtgtgct ggccgcgctg tgcggcatgc tactctgcgc ctctggcctc    60
ttcgccgcgt ctggtgactt ctgtgactcc agcctgtgcc tgaacggtgg cacctgcttg   120
acgggccaag acaatgacat ctactgcctc tgccctgaag gcttcacagg ccttgtgtgc   180
aatgagactg agaggacc atgctcccca aacccttgct acaatgatgc caaatgtctg   240
gtgactttgg acacacagcg tggggacatc ttcaccgaat acatctgcca gtgccctgtg   300
ggctactcgg gcatccactg tgaaaccgag accaactact acaacctgga tggagaatac   360
atgttcacca cagccgtccc caatactgcc gtccccaccc cggcccccac ccccgatctt   420
tccaacaacc tagcctcccg ttgttctaca cagctgggca tggaaggggg cgccattgct   480
gattcacaga tttccgcctc gtctgtgtat atgggtttca tgggcttgca gcgctggggc   540
ccggagctgg ctcgtctgta ccgcacaggg atcgtcaatg cctggacagc cagcaactat   600
gatagcaagc cctggatcca ggtgaacctt ctgcggaaga tgcgggtatc aggtgtgatg   660
acgcagggtg ccagccgtgc cgggagggcg gagtacctga gaccttcaa ggtggcttac   720 agcctcgacg gacgcaagtt tgagttcatc caggatgaaa gcgtggagaa caaggagttt   780
ttgggtaacc tggacaacaa cagcctgaag gttaacatgt tcaacccgac tctggaggca   840
cagtacataa ggctgtaccc tgtttcgtgc caccgcggct gcaccctccg cttcgagctc   900
ctgggctgtg agttgcacgg atgttctgag cccctgggcc tgaagaataa cacaattcct   960
```

-continued

```
gacagccaga tgtcagcctc cagcagctac aagacatgga acctgcgtgc ttttggctgg   1020
tacccccact tgggaaggct ggataatcag ggcaagatca atgcctggac ggctcagagc   1080
aacagtgcca aggaatggct gcaggttgac ctgggcactc agaggcaagt gacaggaatc   1140
atcacccagg gggcccgtga ctttggccac atccagtatg tggcgtccta caaggtagcc   1200
cacagtgatg atggtgtgca gtggactgta tatgaggagc aaggaagcag caaggtcttc   1260
cagggcaact tggacaacaa ctcccacaag aagaacatct tcgagaaacc cttcatggct   1320
cgctacgtgc gtgtccttcc agtgtcctgg cataaccgca tcaccctgcg cctggagctg   1380
ctgggctgtt aa                                                      1392
```

```
<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Asn Ser His Lys Lys Asn Ile Phe Glu Lys Pro Phe Met Ala Arg
 1               5                  10                  15

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgcaggtct cccgtgtgct                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggaaatct gtgaatcagc                                                20
```